US009643000B2

(12) United States Patent
Seip et al.

(10) Patent No.: US 9,643,000 B2
(45) Date of Patent: May 9, 2017

(54) AUTOMATED ULTRASOUND MEDIATED DELIVERY

(75) Inventors: Ralf Seip, Carmel, NY (US); Balasundar Iyyavu Raju, Chester, NY (US); Evgeniy Leyvi, Riverdale, NY (US)

(73) Assignee: Koninklijke Philips N.V., Eindhoven (NL)

( * ) Notice: Subject to any disclaimer, the term of this patent is extended or adjusted under 35 U.S.C. 154(b) by 106 days.

(21) Appl. No.: 14/347,904

(22) PCT Filed: Aug. 29, 2012

(86) PCT No.: PCT/IB2012/054438
§ 371 (c)(1),
(2), (4) Date: Mar. 27, 2014

(87) PCT Pub. No.: WO2013/046076
PCT Pub. Date: Apr. 4, 2013

(65) Prior Publication Data
US 2014/0249469 A1    Sep. 4, 2014

Related U.S. Application Data

(60) Provisional application No. 61/540,232, filed on Sep. 28, 2011.

(51) Int. Cl.
*A61M 37/00* (2006.01)
*A61B 8/08* (2006.01)

(52) U.S. Cl.
CPC ......... *A61M 37/0092* (2013.01); *A61B 8/481* (2013.01)

(58) Field of Classification Search
CPC ................. A61B 8/488; A61B 8/463; A61M 2037/0007; A61N 7/00; A61N 2007/0039
See application file for complete search history.

(56) References Cited

U.S. PATENT DOCUMENTS 5,413,550 A * 5/1995 Castel ............... A61H 23/0245
 601/2
6,264,918 B1 * 7/2001 Johnson ............... A61K 49/223
 424/9.52

(Continued)

FOREIGN PATENT DOCUMENTS

WO    2010020938 A1    2/2010
WO    2013050903 A1    4/2013

OTHER PUBLICATIONS

Ferrara, Katherine et al Ultrasound Microbubble Contrast Agents: Fundamentals and Application to Gene and Drug Delivery, Annual Review of Biomedical Engineering, Sep. 2007, pp. 415-447.

(Continued)

*Primary Examiner* — Bradley Osinski (57) ABSTRACT

Bubble presence within a region is monitored to determine if a predetermined condition is met such as whether the presence is of sufficient magnitude, the bubbles being subject to energizing (240). In some embodiments, the energizing only occurs when time- wise preceded by the determination (S508, S510). The determining can include measuring a grayscale value (104), or assessing the energy carried by a frequency component of the echo signal, in the region in real time. The energizing may occur region-by-region, automatically and without need for user intervention, in a treatment pass (S428) over the regions. The regions (232) in the pass might be subject to respective instances of the energizing without intervening monitoring, or, in another embodiment, to both the determining and the responsive energizing. The determining can be subject to, automatically and without need for user intervention, interruption (S408) and concurrent switching to a next region.

27 Claims, 5 Drawing Sheets

(56) References Cited

U.S. PATENT DOCUMENTS

| | | |
|---|---|---|
| 6,740,039 B1 | 5/2004 | Rafter et al. |
| 2002/0151792 A1 | 10/2002 | Conston et al. |
| 2009/0221902 A1* | 9/2009 | Myhr .................. A61N 7/00 600/411 |
| 2011/0125080 A1 | 5/2011 | Shi |

OTHER PUBLICATIONS

Song, Ji et al "Influence of Injection Site, Microvascular Pressure and Ultrasound Variables on Microbubble-Mediated Delivery of Microspheres to Muscle", Journal of the Americam College of Cardiology, vol. 39, No. 2, 2002, pp. 726-731.

* cited by examiner

AUTOMATED ULTRASOUND MEDIATED DELIVERY

CROSS-REFERENCE TO PRIOR APPLICATIONS

This application is the U.S. National Phase application under 35 U.S.C. §371 of International Application No. PCT/IB2012/054438, filed on Aug. 29, 2012, which claims the benefit of U.S. Provisional Patent Application No. 61/540,232, filed on Sep. 28, 2011. These applications are hereby incorporated by reference herein.

FIELD OF THE INVENTION

The present invention relates to energizing bubbles and, more particularly, to doing so in response to an amount of bubble presence in a region.

BACKGROUND OF THE INVENTION

Ultrasound mediated drug and gene delivery treatment methods using microbubbles are currently being investigated. They have the potential to deliver novel therapeutic agents that have been difficult to deliver in a targeted manner in therapeutically significant doses using conventional techniques. They also offer the potential to treat previously untreatable diseases; reduce side effects, such as toxicity, of current treatments; and reduce dosages of therapeutic agents. One important component of the delivery system is the microbubbles. They enable agent extravasation and transfection when subjected to a suitable ultrasound stimuli. Microbubbles have a limited lifespan when injected in the circulatory system and are typically destroyed shortly after the ultrasound stimulus of sufficient magnitude is applied. Thus, for successful agent delivery, a constant and fresh supply of microbubbles is needed throughout the treatment.

Ultrasound mediated delivery (USMD) of small molecules, genetic material, and other biologicals (from now on referred to collectively as 'therapeutic agents' or simply 'agents') using ultrasound and microbubbles has been shown in pre-clinical studies to enhance delivery and uptake of these agents. Uptake is by the cell via sonoporation and other mechanisms (most not fully understood).

A number of the advantages of USMD treatments are the same that have enabled current ablative-type ultrasound therapies: the treatments are non-invasive, they have the ability to focus energy deep within the body, they have the ability to precisely target within the tissue region of interest while leaving intervening tissues unaffected, and are of a modality that is non-ionizing, allowing repeated applications without limitations imposed by ultrasound dose.

Thus far, most research in USMD has focused on demonstrating feasibility of the technology (typically by showing enhanced uptake of the agent being delivered) in vitro and in animal models in vivo, and on microbubble and delivery vehicle design activities. Less emphasis has been placed on the design of the ultrasound delivery device itself or the design of treatment plans specifically tailored to USMD treatments. While many current pre-clinical results indicate enhanced agent delivery over a wide range of ultrasound pressures and frequencies, pulse durations, pulse repetition frequencies, and pulsing intervals, USMD devices bring with them their own set of custom requirements that need to be addressed prior to their widespread clinical use.

SUMMARY OF THE INVENTION

Microbubbles and the agent to be delivered should be present in the region where the ultrasound energy is to be applied. Without microbubbles, USMD treatments are generally not successful. Thus, it is prudent to verify, prior to sonication, whether an adequate supply of microbubbles is present in the (target) treatment region. During USMD treatments, ultrasound energy is delivered to the same target volume multiple times over the duration of the treatment, in order to transfect the agent in sufficiently large amounts to be therapeutically significant. As different treatment regions have different vasculatures with different blood flow rates, the agent and microbubbles will arrive at these regions in different numbers and at different rates than other regions. This creates a problem, since it is not known exactly a priori when a sufficiently large number of microbubbles and agent is present in any one region to facilitate ultrasound mediated delivery.

Perfusion ultrasound imaging with microbubbles has been used for diagnostic purposes to evaluate perfusion rates in different organs, but it is herein proposed to extend this concept, so that it can also be used to tailor and control the ultrasound energy delivery and treatment plan during ultrasound mediated drug and gene delivery treatments. Using the ideas proposed herein, ultrasound mediated drug/gene delivery treatments can be specifically tailored to the physiology of the target organ for maximum targeted drug/gene extravasation and transfection using ultrasound and microbubbles.

In an aspect of the present invention, an imaging module is configured for monitoring to determine that bubble presence in a region meets a predefined condition. A unit is configured for energizing bubbles within the region to deliver a substance. The device, as a whole, is configured such that the energizing occurs in real time response to the determination that the condition has been met.

In some embodiments, the energizing occurs only when immediately time-wise preceded by the determination.

In a sub-aspect, the determining includes measuring a grayscale value in the region in real time.

In another sub-aspect, the condition includes a magnitude of the presence meeting a predetermined threshold.

In one other sub-aspect, the determining is based on real-time, frequency-specific information derived from imaging of the region.

In an additional sub-aspect, the energizing occurs region-by-region, automatically and without need for user intervention, in a treatment pass over a plurality of regions.

In a further sub-aspect, the plural regions in the pass are subject to respective instances of the energizing without intervening monitoring.

Alternatively, the plural regions in the pass are respectively subject to both the determining and the responsive energizing.

In one further sub-aspect, the region is a current region, and the determining is subject to, automatically and without need for user intervention, interruption and concurrent switching to a next region.

As an additional further sub-aspect, the interruption is, automatically and without need for user intervention, concurrent with adding the current region to a list maintained by the device.

In a yet further sub-aspect, the device is configured for, automatically and without need for user intervention, periodically switching the monitoring from a region not on the list to a region on the list.

In one different sub-aspect, the device is configured for performing the monitoring, by region, in an order that accords priority to regions that, in a prior treatment pass, were on the list.

In yet another sub-aspect, the order is an initial order, subject to the interruption and the concurrent switching.

In a particular aspect, the device is configured for, automatically and without need for user intervention, based on tissue dynamics derived from a result of monitoring that has occurred in a prior treatment pass, adaptively energizing bubbles within the region.

In one other aspect, the adaptive energizing includes adaptively skipping a region.

In a complementary aspect, the device is configured for, automatically and without need for user intervention: a) the monitoring in a current treatment pass; b) deriving, from the monitoring in the current treatment pass, a result; and c) based on the result, completing, without need for further monitoring, a treatment plan.

In a sub-aspect of the above, the result includes a three-dimensional reperfusion map.

In some versions according to a sub-aspect, the device is configured for, automatically and without need for user intervention, making, based on a result derived from the monitoring, an estimate of remaining treatment time and for outputting the estimate to a user of said device.

In some sub-aspects, the energizing delivers acoustic energy.

In other sub-aspects, the monitoring includes performing medical imaging.

In further versions, a computer readable medium embodies instructions executable for the monitoring and energizing, a signal is configured for causing a device to perform the monitoring and energizing, and a method is proposed for generating the signal.

Details of the automated ultrasound mediated delivery technology are set forth further below, with the aid of the following drawings.

DETAILED DESCRIPTION OF EMBODIMENTS

Figure 1:
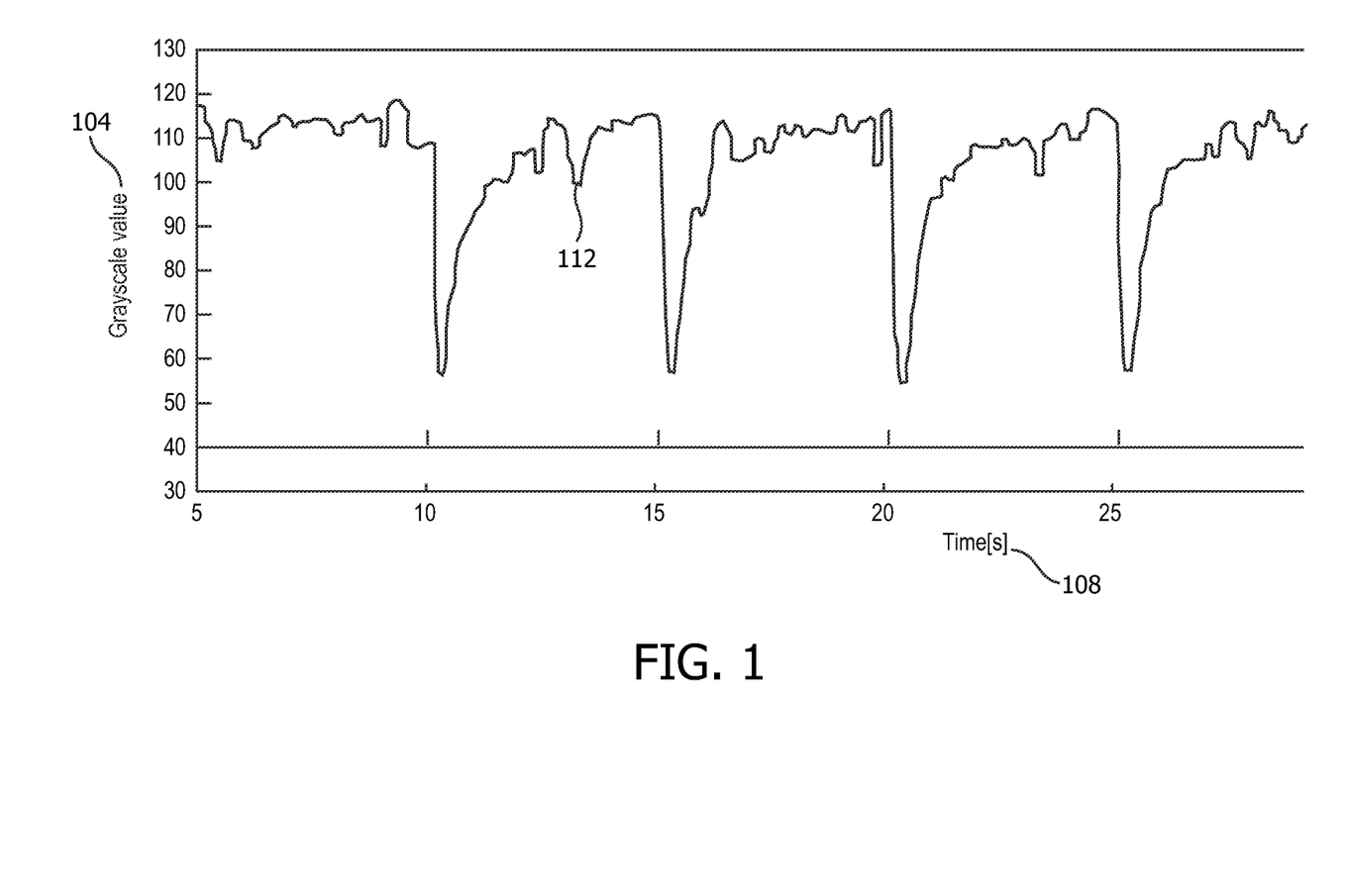
FIG. 1 is a graph of bubble presence, over time, in a region of interest.

FIG. 1 depicts graphically average grayscale value 104 observed via ultrasound, over time 108, in a region of interest (ROI) within a kidney. The ROI includes, or may be coextensive with, a treatment volume, or "treatment region", that is to be treated with a therapeutic agent, such as a drug or gene. Reflection of applied acoustic energy, i.e., ultrasound, is detected by a probe such as a handheld probe. When the ROI tends more to reflect back, rather than absorb, transmit or refract, ultrasound issuing from the probe, the grayscale value of the radiofrequency data acquired is higher. In comparison to body tissue, bubbles, such as microbubbles or nanobubbles, are particularly good reflectors of ultrasound. Injected bubbles disseminate throughout the vasculature and are intended to arrive at the ROI, provided sufficient vasculature exists there. The higher values 104 in the grayscale graph 112 correspond to times 108 when bubble presence in the ROI is greater. The bubbles can be microbubbles or nanobubbles for instance, although microbubbles will be referred to hereinafter. An exemplary bubble diameter range is from 100 nanometers (nm) to 50 microns ($\mu$m). The microbubbles are associated with a nearby therapeutic agent such as a drug or gene. The agent may be attached to the outside of the microbubble surface, embedded within the surface, carried within the microbubble, or be coinjected with the microbubble. By applying ultrasound to energize the microbubbles in the treatment region, the agent is delivered for its therapeutic purpose. This is known as ultrasound mediated delivery (USMD). The energization can involve thermal effects to release the agent; however, for a particular type of USMD proposed herein, the energization instead largely avoids thermal effects. The release mechanism operates instead by oscillating and bursting the microbubbles. This is achieved with shorter pulse lengths and higher acoustic pressures than would be used for thermal effects. An additional result of the oscillating is that it can cause nearby cell membranes to become porous, temporary porosity allowing the transfection of the agent into the cell. Thus, the agent is more effectively delivered, or, in some cases, delivery would be incomplete without the sonoporation affording temporary porosity.

To deliver an effective dose of the agent, however, a sufficient amount of bubble presence is needed in the treatment region.

Referring again to FIG. 1, at around the 10 second mark, an ultrasound pulse, or series of pulses, of sufficient length and amplitude are delivered to destroy microbubbles in the treatment region. The consequent, sharply reduced echogeneity in the ROI causes a precipitous drop in grayscale value.

After about 2 seconds, enough microbubbles upstream in the vasculature "wash in" to the treatment region and replenish the microbubbles in the treatment region. The duration of replenishment, or "reperfusion", is logged by a device which may be an ultrasound device such as a scanner with an ultrasound probe.

A number of treatment passes over an entire treatment area may be required to collectively deliver enough agent to each treatment region; accordingly, logging replenishment durations is useful in predicting subsequent replenishment rates in the respective treatment regions.

The logged values also carry diagnostic value. In particular, necrotic tumor cores, for example, would take significantly longer time to re-perfuse compared to highly vascularized tumors or tissues, or alternatively might never re-perfuse.

Sending out additional therapeutic pulses while replenishment is still underway would not contribute significantly to additional agent extravasation and transfection, because the volume of microbubbles that is required is no longer present in the ROI. Delivering pulses regardless of microbubble presence in the ROI would likely only decrease treatment efficiency, because new microbubbles being washed into the treatment region would be destroyed before reaching the concentration needed for effective agent delivery.

On the other hand, waiting too long between therapeutic pulses would increase the total treatment time 108. It would also lead to poor efficacy of treatment in gene delivery applications, since the agent would be destroyed over a short period of time by immune mechanisms in the blood.

In this context it is noted again here that replenishment durations naturally vary from one target tissue to another, due to differences in the local vasculature.

It is accordingly desired to tailor a treatment plan, based on tissue target type using ultrasound feedback.

Figure 2:
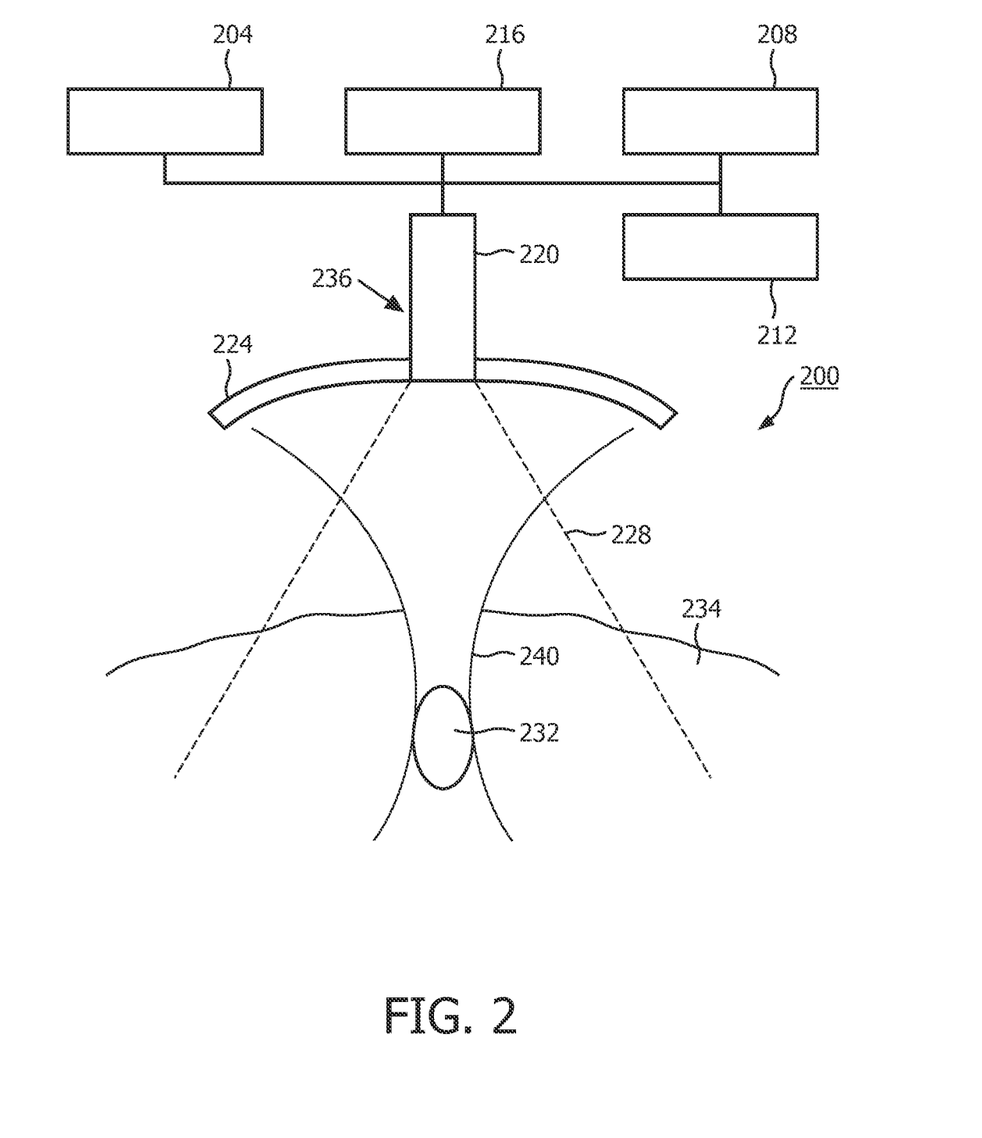
FIG. 2 is a schematic diagram of an automatic USMD device.

A device 200, as shown in FIG. 2, for implementing the technology proposed herein might include, in addition to a medical imaging module 204 and therapy unit 208, an injection apparatus 212 for administering, by injection, microbubbles and agent, and a controller 216 for these components 204, 208, 212. The microbubbles and agent may be pre-configured so that the microbubbles carry the agent. Alternatively, the microbubbles and agent are co-injected, with their mixture occurring before administration or internally after administration. Or, in some cases, the microbubbles and agent are injected separately, to avoid adverse chemical interaction as discussed in the commonly-assigned patent application entitled "Assays for Ultrasound Mediated Delivery." As an alternative to automatic administration by the controller 216, the microbubble and agent are administered under manual control by the clinician.

Both the imaging module 204 and the therapy unit 208 operate or comprise respective ultrasound transducers, or ultrasound transducer arrays, 220, 224.

The medical imaging in two or three dimensions provides a field of view (FOV) 228 that covers a treatment region 232, which in the case shown is a focal zone or "focal spot" within body tissue 234. The imaging may be for example in B-mode, or in contrast mode. The contrast mode may include non-linear imaging methods, such as harmonic imaging, pulse inversion imaging, and power modulated pulse inversion imaging. In order to not destroy bubbles with the imaging beam, it is issued with low mechanical-index (MI). Typically, the MI is less than or equal to 0.1.

The ultrasound treatment beam is focused, weakly focused or unfocused. In any event, the therapeutic ultrasound can be delivered by a single element, or by a one- or two-dimensional array.

The imaging transducer 220 and therapy transducer 224 can be part of the same probe 236, and confocal as shown in FIG. 2. Alternatively, a single transducer can operate in a therapy mode and in an imaging mode. It is not expected, and most of the time not possible, to image at the same time that acoustic energy 240 in the form of therapeutic pulses is being delivered. This is because the amplitudes of the therapeutic pulses are larger than those of the imaging pulses, causing interference with the monitoring function. Thus, imaging/monitoring and delivering therapeutic pulses are mutually exclusive events. A switch can be added to the device 200 to select between the functionality of the transducer, from an imaging mode used during monitoring to a therapy mode used during energy delivery.

The device 200 further includes a registration mechanism by which it is assured that the FOV covers the field of action of the therapy transducer 224, and that a one-to-one registration between the coordinate systems of the imaging and therapy transducers 220, 224 is established. Even with the confocal setup in FIG. 2, an adjustment to axial registration may be appropriate. To fine tune registration, a small amount of microbubbles may be injected at the outset, with imaging and a display screen active. The clinician, or other user of the device 200, can then see if oscillation occurred where expected, and make any needed change to parameters associated with the imaging and/or therapy beams. This can be done by pointing to (with a touch-sensitive screen) or navigating to (as by manipulating a mouse) a corresponding point in the displayed image.

A treatment plan execution algorithm, executed by the controller 216 for example, maximizes the ultrasound mediated transfection and delivery of agents based on real-time feedback obtained from the imaging transducer 220, and an associated imaging analysis function, and a priori information. The a priori information includes, but is not limited to: injected microbubble concentration, in vivo microbubble half-life, microbubble oscillation and destruction pressures and treatment repeats needed to achieve a therapeutically significant extravasation and transfection for the target tissue based on clinical trial data and pre-clinical studies, typical tissue attenuation, therapy transducer focal zone size and shape, and therapy transducer focusing capabilities. The algorithm can be received by the controller 216 by wire input, or wirelessly via an antenna and from a remote transmitting antenna. In either case, the signal to be transmitted is generated by appropriately varying an electrical current. Other control information, or data, can likewise be embodied within the signal.

The overall goals of the treatment plan execution algorithm are to: (i) ensure that the therapeutic ultrasound is only applied to the current (target) region 232 when microbubbles are present in the required amount; and (ii) deliver therapeutic ultrasound to the current region in the required dose and in the shortest time feasible.

To expedite the USMD procedure, an unfocused therapy beam may be applied. It covers a much larger volume than the typical focal region. Thus fewer separate therapy exposures are required in carrying out the overall treatment plan. This saves time, with the additional consequent benefits of fewer chances for error due to patient or clinician movement, and cost savings as a result of the reduced service time.

Figure 3:
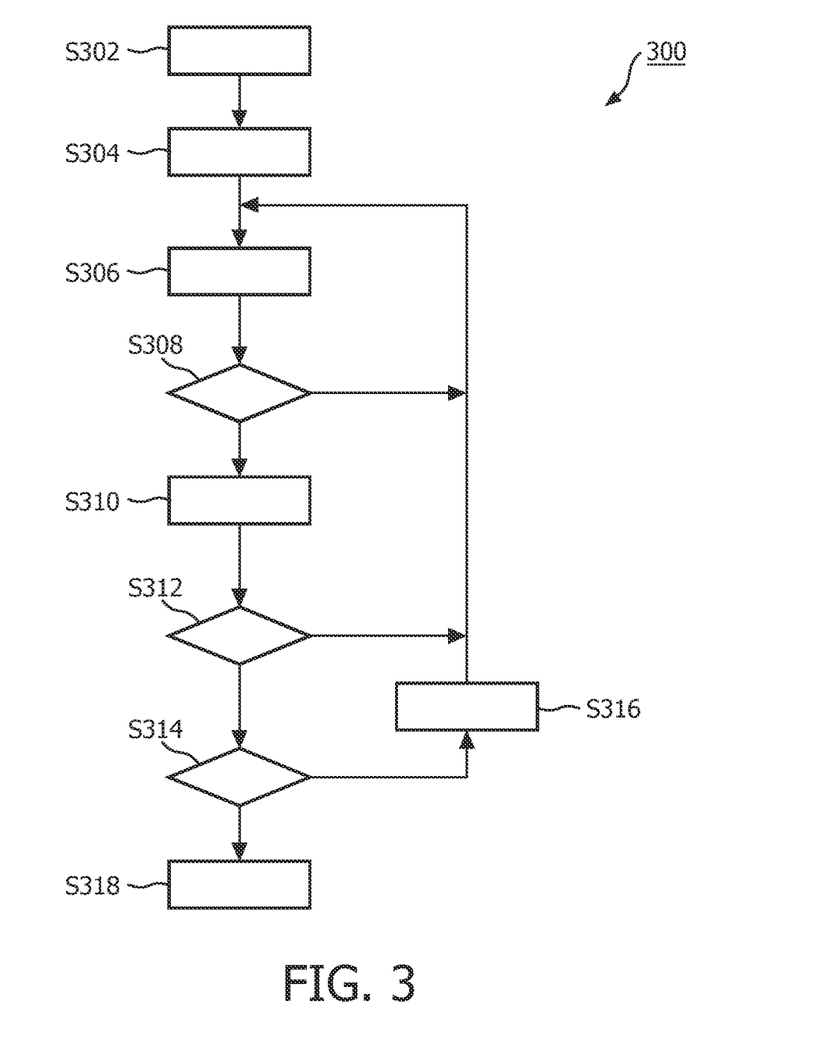
FIG. 3 is a flow chart of treatment plan using an unfocused therapy transducer.

An exemplary unfocused-therapy-beam procedure 300 in FIG. 3 commences, after the treatment plan is defined (step S302), with infusion of microbubbles and agent to be delivered (step S304). As part of treatment monitoring, readings derived from the imaging for the ROI are taken (step S306). The condition to be met can, for example, involve attainment of threshold grayscale value, or mean grayscale value over the ROI. Alternatively, the determination as to whether the condition is met might be based on real-time, frequency-specific information derived from imaging of the ROI. The information may include the strength of a particular frequency in the echo received from a ROI, the emergence of a certain frequency band, etc., which would be generated by the harmonic echo from the microbubbles once present in the ROI at a sufficiently high concentrations, for example. Once the predefined condition is met (step S308), a preestablished therapeutic ultrasound pulse is issued (step S310). This can occur automatically and without the need for user intervention. The pulse oscillates and bursts the microbubbles in the current treatment region 232. This leads to agent extravasation and transfection. Query is then made as to whether a targeted dose for the current treatment region, which is normally the same for each treatment region 232, has been reached. Each iteration of energizing the current treatment region 232 may be assumed to release a particular amount of agent for uptake in the region, in which case that amount is multiplied by the number of iterations so far. Alternatively, if the imaging rate during monitoring is relatively low, actual bubble presence in the treatment region 232 may be calculated based on the grayscale value acquired just before energization. Each of these bubble presence values can be summed to arrive at an estimate of accumulated dosage. If the total targeted dosage for the current treatment region 232 has not yet been met (step S312), processing returns to step S306, or alternatively to step S302. Otherwise, if the total targeted dosage for the current treatment region 232 is now met (step S312) and a next treatment region remains (step S314), the unfocused transducer is moved to point to that next treatment region (step S316). If the probe 236 is handheld, the clinician makes this move manually. The transducer movement could also be mechanical, or accomplished by switching to a second probe already in place. On the other hand, if there is no next treatment region 232 (step S314), the infusion is halted and the procedure is terminated (step S318).

Figure 4:
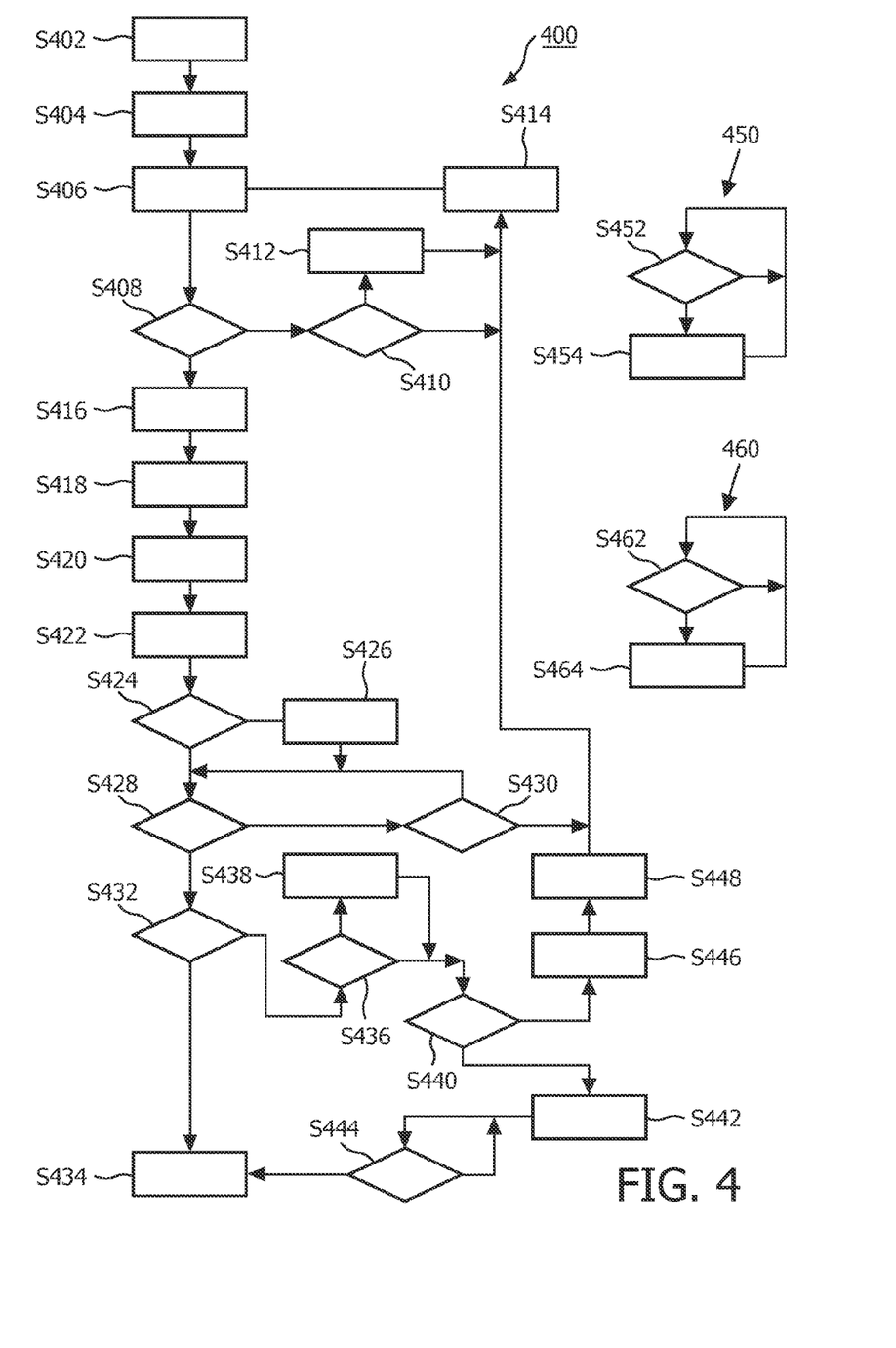
FIG. 4 is a flow chart of treatment plan execution using a focused or weakly focused therapy transducer.

A focused-or-slightly-focused-therapy-beam procedure 400, represented by FIG. 4, by way of illustrative and non-limitative example, more precisely delivers the agent to the intended treatment regions 232. This avoids side effects in adjoining tissue and is especially appropriate for an overall small treatment area divisible into separate treatment regions 232. The embodiment shown incorporates a number of features for minimizing total treatment time. The treatment region 232 typically has a size defined by that of the focal spot of the therapy transducer 224.

As in the embodiment of FIG. 3, treatment commences, after the treatment plan is defined (step S402), with infusion of microbubbles and agent to be delivered (step S404).

As part of treatment monitoring, imaging readings for the ROI are taken (step S406).

If the predefined condition is not met, i.e., indicative of insufficient local bubble presence (step S408), query is made as to whether the current treatment region 232 is on a list maintained by the device 100 (step S410). The list is made up of treatment regions 232 that have not yet been energized during the current pass, i.e., and consequently remain to be energized. If the current treatment region 232 is not on the list (step S410), it is added to the list (step S412). In either event, the therapy focus shifts to the next treatment region 232 in the current treatment pass (step S414) and processing returns to step S406. The fact that the condition was not met in step S408 guarantees that that next treatment region 232 exists, i.e., some treatment region qualifies as the next treatment region even if only the current region is left and is thus regarded as the "next" treatment region. More generally, whether that next treatment region 232 is picked from the list or from treatment regions not on the list depends on whether list mode is "on." Initially, that is in steps 402 and 404, list mode is "off", since there is not yet any list (for the current pass). The purpose of the list is to minimize the total time spent in treatment. Utilizing the list avoids waiting in the type of loop shown in S306 to S308, unnecessarily for regions to replenish with microbubbles while other regions would already meet this condition and be deemed ready to receive treatment. Yet, the list can be returned to, periodically for instance, for monitoring and result dependent region-energizing. This return and the switch back are automatic and performed without the need for user intervention. Notably, the treatment plan adapts to local perfusion characteristics of the target tissue. In particular, regions with slower perfusion, and hence slower microbubble reperfusion, will require longer treatment time, i.e., uninterrupted clock time from the start of monitoring for the treatment region 232 until the completion of treatment for the region. However, as in the previous embodiment, of FIG. 3, all treatment regions 232 ultimately receive the same dose. It is noted here too that the S406-S414 loop operates automatically and without the need for user intervention. It efficiently defers treatment for regions 232 that are not, at present, ready for dosage delivery by means of the microbubbles and redirects current treatment to regions that are found to be ready.

If, on the other hand, the predefined condition is met (step S408), the bubble replenishment delay is logged (step S416), a pulse is applied (step S418), oscillating bubbles burst (step S420), and therapeutic agent is delivered to the current treatment region 232 (step S422).

Query is made as to whether the current treatment region 232 is on the list (step S424). If the current treatment region is on the list (step S424), it is now removed from the list (step S426).

In either event, query is now made as to whether a next treatment region 232 exists in the current pass (step S428).

If a next treatment region 232 exists in the current pass (step S428), query is made, automatically and without the need for user intervention, as to whether to skip that next treatment region (step S430). If, for example, that next treatment region 232 has been identified based on a previous treatment pass, or a plurality of previous treatment passes, as exhibiting a bubble replenishment duration that is sufficiently short, this could indicate that the treatment region 232 is populated mostly by larger vessels with higher blood flow. Thus, treating this region would not necessarily increase the efficacy of the treatment, and the region can be skipped.

If it is here decided that this next treatment region 232 is to be skipped (step S430), processing returns to step S428.

If, to the contrary, it is here decided that this next treatment region 232 is not to be skipped (step S430), processing branches back to step S414 with the therapy focus shifting to this next treatment region. The shifting is done by electronic steering automatically and without the need for user intervention. Alternatively, the shifting can be done manually or mechanically.

If, on the other hand, a next treatment region 232 no longer exists in the current treatment pass (step S428), query is made as to whether the agent- or ultrasound-dose is still incomplete for at least some treatment region (step S432).

If the dose is complete for all treatment regions 232 (step S432), the infusion is halted and the procedure is terminated (step S434).

If, to the contrary, the dose is incomplete for some treatment region 232 (step S432), query is made as to whether this is the first treatment pass (step S436). If it is not the first treatment pass (step S436), an estimate of remaining treatment time is indicated to a user of the device 100 (step S438). The treatment time execution algorithm can make this estimate based on information, e.g., observed values of treatment-region-specific replenishment duration and list processing duration, collected during the first treatment pass. The estimate can also take into account the experience of any previous treatment pass after the first treatment pass.

Query is then made as to whether a three-dimensional (3D) reperfusion map option was selected by the user (step S440). The user selection can be made at this point, or may have been made earlier, such as at the outset of the USMD procedure thereby allowing processing here to proceed automatically and without the need for user intervention. The reperfusion map option allows treatment to proceed expeditiously from this point forward. Further bubble presence monitoring is foregone. However, at least the experience of the first treatment pass operates to shorten overall time-wise the remaining part of the treatment. That experience, i.e., the reperfusion map, includes replenishment duration information acquired, treatment region-by-treatment region, during the first treatment pass. Accordingly, the remainder of the treatment proceeds automatically and without the need for user intervention, foregoing the feedback that would otherwise be utilized in closed loop operation.

If the reperfusion map option is or was selected by the user (step S440), the treatment proceeds to completion based on the reperfusion map and without need for further bubble monitoring (step S442). Once dosage is complete for all treatment regions 232 (step S444), the infusion is halted and the procedure is terminated (step S434).

If, on the other hand, the reperfusion map option is not selected (step S440), the next treatment pass becomes the current treatment pass, i.e., the treatment pass counter is bumped up (step S446). In addition, each treatment region 232 is assigned an initial priority based on the list in the previous pass (step S448). Thus, treatment regions 232 that were on the list are, or tend to be, accorded higher priority than treatment regions not on the list. Regions 232 that were on the list will tend to be mutually nearby, all sharing the same or similar local vascularity evidenced by the slow reperfusion. If processing region-to-region proceeds upstream, energizing of one region 232 will not tend to affect replenishment duration for another. Sometimes, however, it is impractical or infeasible to determine whether the processing proceeds upstream or not. Accordingly, energizing one on-list region 232, i.e., on the list in the previous treatment pass, may adversely affect replenishment duration for a nearby on-list region. Accordingly, it is prudent to begin processing the on-list regions 232 early. That way, there are potentially more opportunities to catch the relatively slow-reperfusing regions 232 at a good time. Another possible refinement is to reduce initial priority for regions 232 that would otherwise be accorded high priority but were actually energized toward the end of the most recent treatment pass. Similar considerations can be made for other regions based on the same principle. Processing returns to step S414.

Two processes execute in parallel with the above procedure 400.

A list mode process 450, queries as to whether the list mode is to be switched (step S452). When it is ready to be switched (step S452), the switch is made (step S454).

A region skipping process 460 queries as to whether the replenishment rate observed in previous treatment pass, or treatment passes, exceeds a pre-specified threshold (step S462). If the threshold is exceeded, skipping is set "on" for the respective treatment region 232 (step S464).

Figure 5:
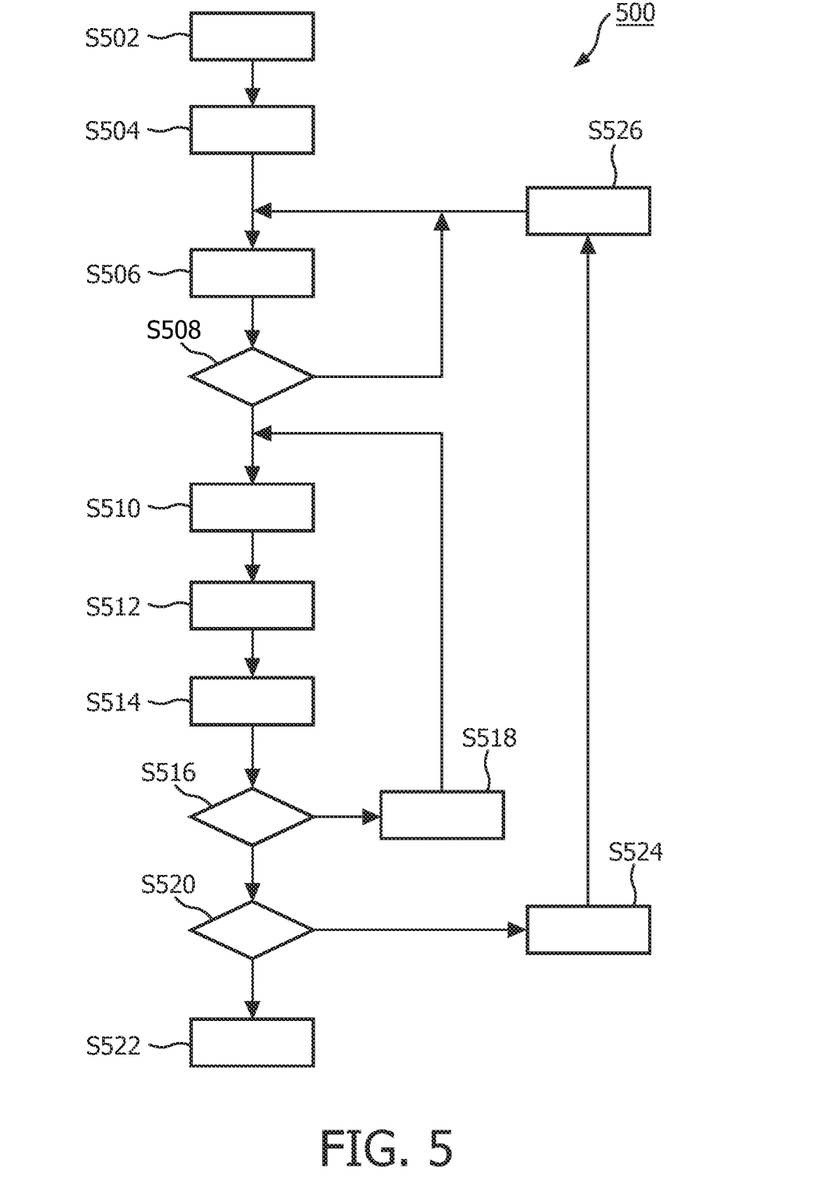
FIG. 5 is a flow chart of treatment plan execution using a focused or weakly focused therapy transducer with reduced monitoring.

An alternative treatment plan 500, represented in FIG. 5, for a focused or weakly focused therapy transducer 224 reduces the amount of region monitoring, but can retain effectiveness in dosage delivery by treating regions in an upstream order with respect to blood flow. The first two steps (S502, S504) are analogous to the initial steps S302, S304 in FIG. 3 and the initial steps S402, S404 in FIG. 4. However, they may be accompanied, in any order, by a blood flow direction determination. First, the probe 236 is manipulated, e.g., manually, angularly and/or laterally, and interactively with a display or audio feedback, using a relatively wide FOV, treatment plan-wise, to detect sufficient Doppler power. A directional reading of blood flow is obtained, as by color Doppler. The transducer focus is then moved, electronically, to an initial treatment region 232 relatively downstream of the flow, if such a starting point is medically advisable or feasible.

As part of treatment monitoring, imaging readings for the ROI are taken (step S506).

Once the predefined condition is met (step S508), a pulse is applied (step S510), oscillating bubbles burst (step S512), and therapeutic agent is delivered (step S514).

If a next treatment region 232 remains in the current treatment pass (step S516), the therapy focus is moved to that next treatment region (step S518), and processing returns to step S510.

Otherwise, if no next treatment region 232 remains in the current treatment pass (step S516), query is made as to whether the dosage is complete (step S520).

If the dosage is complete (step S520), the infusion is halted and the procedure is terminated (step S522).

Otherwise, if dosage is not complete (step S520), the next treatment pass becomes the current treatment pass (step S524), the therapy focus moves to the first treatment region 232 (S526) and processing branches back to step S506.

Time expended in USMD, and thus cost to the patient and the possibility of treatment error due to patient/clinician movement, are minimized by a set of automated procedures. The latter include a procedure for unfocused ultrasound for treating large volumes at a time. Among the procedures too, are those for focused or weakly focused ultrasound transducers, these procedures featuring updatable sensitivity to the local anatomy, thereby expediting the entire procedure. The procedures can be automated and carried out without the need for user intervention; yet, like conventional USMD, they are medically safe, non-invasive and performed without ionizing radiation.

Bubble presence within a region is monitored to determine if a predetermined condition is met such as whether the presence is of sufficient magnitude, the bubbles being subject to energizing. Ultrasonic methods to determine microbubble presence are known in the art and include B-mode ultrasound imaging, or any of the nonlinear microbubble response based imaging including pulse inversion, power Doppler, and contrast sequence imaging. In some embodiments, the energizing only occurs when timewise preceded by the determination. The determining can include measuring a grayscale value, or assessing the energy carried by a frequency component of the echo signal, in the region in real time. The energizing may occur region-by-region, automatically and without need for user intervention, in a treatment pass over the regions. The regions in the pass might be subject to respective instances of the energizing without intervening monitoring, or, in another embodiment, to both the determining and the responsive energizing. The determining can be subject to, automatically and without need for user intervention, interruption and concurrent switching to a next region. The interruption is, automatically and without need for user intervention, concurrent with adding the current region to a list maintained.

Although methodology of the present invention can advantageously be applied in providing USMD for a human or animal subject, the scope of the present invention is not so limited. More broadly, techniques disclosed herein are directed to USMD to body tissue, in vivo, in vitro or ex vivo, and even to non-medical substance delivery technology.

While the invention has been illustrated and described in detail in the drawings and foregoing description, such illustration and description are to be considered illustrative or exemplary and not restrictive; the invention is not limited to the disclosed embodiments.

For example, the reperfusion map can be of fewer than three dimensions, and it, as well as the remaining time indicator, can be adapted for the alternative treatment plan 500 with reduced monitoring. Also, the device 200 portrayed in FIG. 2 is exemplary. The device 200, as claimed, may more broadly be implemented in one or more integrated circuits.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. Any reference signs in the claims should not be construed as limiting the scope.

A computer program can be stored momentarily, temporarily or for a longer period of time on a suitable computer-readable medium, such as an optical storage medium or a solid-state medium. Such a medium is non-transitory only in the sense of not being a transitory, propagating signal, but includes other forms of computer-readable media such as register memory, processor cache, RAM and other volatile memory.

A single processor or other unit may fulfill the functions of several items recited in the claims. The mere fact that certain measures are recited in mutually different dependent claims does not indicate that a combination of these measures cannot be used to advantage.

What is claimed is:

1. A device comprising:
   an imaging module configured for monitoring, according to each iteration of a number of iterations of a treatment plan, a current treatment region of a plurality of treatment regions over an entire treatment area, to determine whether bubble presence in the current treatment region meets a predefined threshold of a magnitude of said bubble presence; and
   a unit configured for energizing bubbles within said current treatment region to deliver a substance,
   wherein said energizing bubbles (i) occurs in real time response to a determination that said predefined threshold has been met for the current treatment region, and (ii) is skipped for the current treatment region in real time response to the determination that said predefined threshold has not been met, further wherein subsequently the imaging module and the energizing unit proceed with a next treatment region until all of the plurality of treatment regions of the entire treatment area for the number of iterations of the treatment plan receive deliver of the substance, and wherein if said energizing bubbles is skipped for the current treatment region in response to the determination that said predefined threshold has not been met, the imaging module and the energizing unit are configured to return to the current treatment region to determine whether bubble presence in the current treatment region meets the predefined threshold after determination of bubble presence is made for the next treatment region.

2. The device of claim 1, wherein further said energizing bubbles within said current treatment region occurs only when immediately time-wise preceded by the determination.

3. The device of claim 1, wherein monitoring to determine comprises measuring a grayscale value in said current treatment region in real time.

4. The device of claim 1, wherein monitoring to determine is based on real-time, frequency-specific information derived from imaging of said current treatment region.

5. The device of claim 1, wherein energizing occurs region-by-region, automatically and without need for user intervention, in a treatment pass over the plurality of treatment regions.

6. The device of claim 5, wherein the plurality of treatment regions in said treatment pass are subject to respective instances of said energizing without intervening monitoring.

7. The device of claim 5, wherein the plurality of treatment regions in said treatment pass are respectively subject to both the determining and the responsive energizing).

8. The device of claim 7, further wherein said determining is subject to, automatically and without need for user intervention, interruption and concurrent switching to a next treatment region.

9. The device of claim 8, further wherein said interruption is, automatically and without need for user intervention, concurrent with adding said current treatment region to a list maintained by said device.

10. The device of claim 9, further comprising a controller for, automatically and without need for user intervention, periodically switching said monitoring from a treatment region not on said list to a treatment region on said list.

11. The device of claim 9, further wherein the imaging module performs said monitoring, by treatment region, in an order that accords priority to the plurality of treatment regions that, in a prior treatment pass, were on said list.

12. The device of claim 11, wherein said order comprises an initial order, subject to said interruption and said concurrent switching.

13. The device of claim 1, further wherein the unit, automatically and without need for user intervention, based on tissue dynamics derived from a result of monitoring that has occurred in a prior treatment pass, adaptively energizes bubbles within said current treatment region.

14. The device of claim 13, further wherein the unit adaptively skips the current treatment region.

15. The device of claim 1, further comprising a controller for, automatically and without need for user intervention: a) initiating said monitoring in a current treatment pass; b) deriving, from said monitoring in said current treatment pass, a result; and c) based on said result, completing, without need for further monitoring, the treatment plan.

16. The device of claim 15, wherein said result comprises a three-dimensional reperfusion map.

17. The device of claim 1, further comprising a controller for, automatically and without need for user intervention, making, based on a result derived from said monitoring, an estimate of remaining treatment time and for outputting said estimate to a user of said device.

18. The device of claim 1, wherein said energizing comprises delivering acoustic energy.

19. A non-transitory computer readable medium embodied with instructions executable by a processor for carrying out a series of acts for a substance delivery device, the acts comprising:
   monitoring, according to each iteration of a number of iterations of a treatment plan, a current treatment region of a plurality of treatment regions over an entire treatment area, to determine whether bubble presence in the current treatment region meets a predefined magnitude of said bubble presence; and
   energizing bubbles within said current treatment region to deliver a substance,
   wherein said energizing bubbles (i) occurs in real time response to a determination that said predefined magnitude has been met for the current treatment region, and (ii) is skipped for the current treatment region in real time response to the determination that said predefined magnitude has not been met, further wherein subsequently the monitoring and the energizing proceed with a next treatment region until all of the plurality of treatment regions of the entire treatment area for the number of iterations of the treatment plan receive deliver of the substance, and wherein if said energizing bubbles is skipped for the current treatment region in response to the determination that said predefined threshold has not been met, returning to the current treatment region to determine whether bubble presence in the current treatment region meets the predefined threshold after determination of bubble presence is made for the next treatment region.

20. The non-transitory computer readable medium of claim 19, wherein further said energizing bubbles within said current treatment region occurs only when immediately time-wise preceded by the determination.

21. The non-transitory computer readable medium of claim 19, wherein monitoring to determine comprises measuring a grayscale value in said current treatment region in real time.

22. The non-transitory computer readable medium of claim 19, wherein monitoring to determine is based on real-time, frequency-specific information derived from imaging of said current treatment region.

23. The non-transitory computer readable medium of claim 19, wherein said energizing occurs region-by-region, automatically and without need for user intervention, in a treatment pass over the plurality of treatment regions.

24. The non-transitory computer readable medium of claim 23, wherein the plurality of treatment regions in said treatment pass are subject to respective instances of said energizing without intervening monitoring.

25. The non-transitory computer readable medium of claim 23, wherein the plurality of treatment regions in said treatment pass are respectively subject to both the determining and the responsive energizing.

26. The non-transitory computer readable medium of claim 25, further wherein said determining is subject to, automatically and without need for user intervention, interruption and concurrent switching to a next treatment region.

27. The non-transitory computer readable medium of claim 26, further wherein said interruption is, automatically and without need for user intervention, concurrent with adding said current treatment region to a list maintained by said device.

* * * * *